United States Patent [19]

Chang et al.

[11] 4,420,430

[45] Dec. 13, 1983

[54] METHOD FOR PREPARING ORGANO GERMANIUM PROPIONIC ACID DERIVATIVES

[75] Inventors: Ching-Te Chang, Taipei; Lian-Tze Lee, Hsinchu, both of Taiwan; Hsueh-Ling Su, St. Paul, Minn.

[73] Assignee: Industrial Technology Research Institute, Hsinchu, Taiwan

[21] Appl. No.: 344,375

[22] Filed: Feb. 1, 1982

[51] Int. Cl.$^3$ .............................................. C07F 7/30
[52] U.S. Cl. .............................................. 260/429 R
[58] Field of Search ................................... 260/429 R

[56] References Cited

U.S. PATENT DOCUMENTS

| | | | |
|---|---|---|---|
| 3,689,516 | 9/1972 | Asai et al. | 260/429 R |
| 3,812,167 | 5/1974 | Pahk | 260/429 R |
| 4,066,678 | 1/1978 | Sato et al. | 260/429 R |
| 4,271,084 | 6/1981 | Ishikawa et al. | 260/429 R |
| 4,281,015 | 7/1981 | Ishikawa et al. | 260/429 R X |

*Primary Examiner*—Helen M. S. Sneed
*Attorney, Agent, or Firm*—Bert J. Lewen

[57] ABSTRACT

Germanium tetrachloride is reduced with hypophosphorous acid or its salt in hydrochloric acid, or lower alcohol, or lower alcoholic hydrochloric acid solution. The reaction mixture is then reacted with acrylic acid derivatives and further hydrolyzed to the desired organo germanuim propionic acid derivatives.

17 Claims, No Drawings

METHOD FOR PREPARING ORGANO GERMANIUM PROPIONIC ACID DERIVATIVES

This invention relates to a method for the preparation of organo germanium propionic acid derivatives from germanium tetrachloride.

K. Asai and others have found that germanium chloroform (HGeCl$_3$) can react with acrylonitrile or acrylic acid to give bis-beta-carboxy ethyl germanium sesquioxide, a product that proved to have the following significant pharmacological effects:

(a) Ehrich ascites tumour growth inhibition (U.S. Pat. No. 3,689,516, K. Asai, Sept. 5, 1972).

(b) Curing and life prolongation effect on rat ascites hepatoma AH44 and AH66 and on ACI rats BC47 tumour.

(c) Hypertension (high blood pressure) treatment (U.S. Pat. No. 3,793,455, K. Asai et al, Feb. 19, 1974).

(d) Inhibition of amyloidosis occurrence.

(e) Treating infections caused by viral cells and protozoa.

(f) Plant growth rate acceleration.

(g) Treating various diseases in clinical tests.

In the prior art, germanium sesquioxide propionic derivatives are prepared by the following scheme (U.S. Pat. Nos. 3,689,516 and 3,793,455; Japanese Pat. No. 46-2498, Japan Gaishi K.K., Jan. 21, 1974):

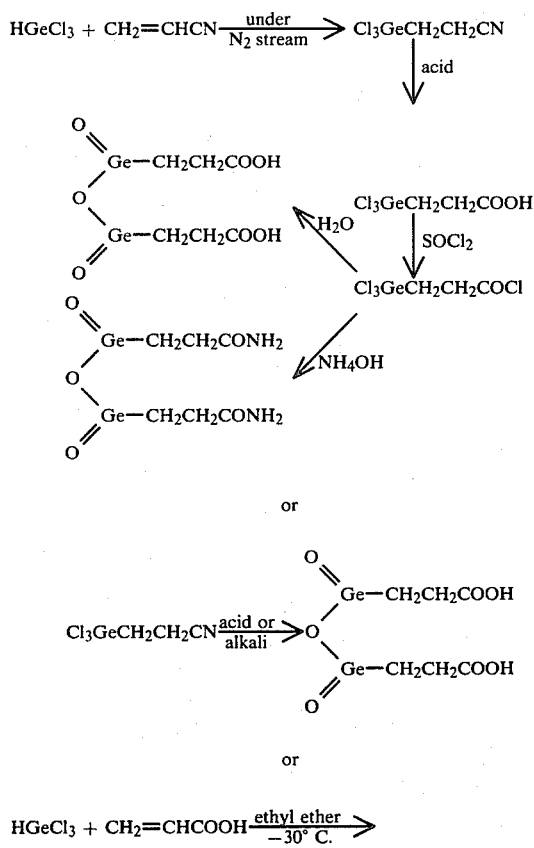

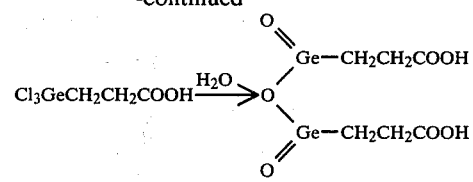

In all these processes, HGeCl$_3$, is employed as the starting germanium material; which is usually obtained as follows:

(a) GeS + HCl → HGeCl$_3$ (b) Ge(OH)$_2$ + HCl → HGeCl$_3$ (c) GeCl$_2$ + HCl → HGeCl$_3$.

Germanium compounds used in the above processes are unstable in nature and therefore difficult to handle. As a result, HGeCl$_3$ is not readily available for application.

Ung Soo Park has suggested the preparation of bis-beta-carboxy ethyl germanium sesquioxide from germanium dioxide (U.S. Pat. No. 3,812,167, May 21, 1974). The process includes:

GeO$_2$ + HCl → GeCl$_4$

GeCl$_4$ + NaH$_2$PO$_4$ → HGeCl$_3$

HGeCl$_3$ + NH$_4$OH → Ge(OH)$_2$ ↓

Ge(OH)$_2$ + HCl → HGeCl$_3$

HGeCl$_3$ + CH$_2$=CHCN → Cl$_3$GeCH$_2$CH$_2$CN

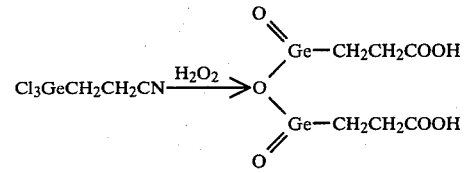

The above reactions however are found to be incapable of providing the said compound due to the fact that the monobasic sodium phosphate has no potentiality to reduce germanium dioxide.

It is therefore the object of the present invention to overcome the defects of the above-mentioned methods by effectively using commonly and easily available starting materials. In the present process, germanium tetrachloride is reduced by means of hypophosphorous acid or its salt in the presence of hydrochloric acid, or a lower alcohol or lower alcoholic hydrochloric acid. It is then, in situ, reacted with an acrylic-type derivative followed by hydrolysis to form organo germanium propionic acid derivatives.

In the first step in the method of the invention germanium tetrachloride in lower alcohol or in hydrochloric acid solution is readily reduced by hypophosphorous acid to a mixture of germanium phosphite and germanium chloride. This invention utilizes the germanous compound and hydrochloric acid in aqueous solution and/or in lower alcoholic solutions which are compatible with water. The reactant thus formed tends to react with acrylic derivatives, and provides a mixture of organo germano chloride and phosphite. The reaction mixture can be hydrolyzed in situ to yield the organo germanium sesquioxide derivatives as follows:

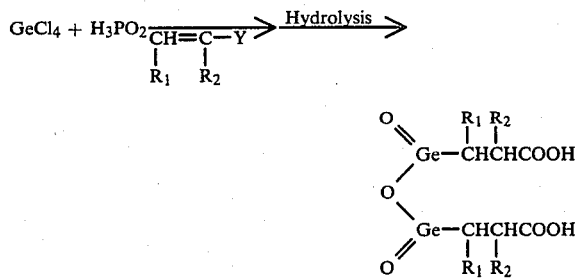

wherein Y stands for COOH, COOR (R being lower alkyl), $CONH_2$ or CN, and $R_1$ and $R_2$ stand independently for H or lower alkyl.

Accordingly, the invention is directed to a process for preparing an organo germanium sesquioxide derivative of the following formula (II):

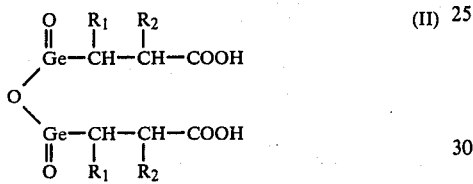

where $R_1$ and $R_2$ are independently hydrogen or lower alkyl involving the steps of:

(i) contacting germanium tetrachloride with hypophosphorous acid (added as such, or generated in situ from a salt thereof by the action of hydrochloric acid and/or a lower alcohol) whereby the germanium tetrachloride is reduced, (ii) thereafter adding to the reaction mixture an acrylic acid derivative of the following formula (I):

where $R_1$ and $R_2$ are as previously defined and Y is COOH, COOR (R being lower alkyl,) $CONH_2$ or CN, and (iii) hydrolyzing the product of step (ii) whereby the said compound of formula II is formed.

The lower alcohol employed in step (i) is ordinarily a $C_1$–$C_3$ alkanol. This step is suitably carried out at elevated temperature, for example at refluxing temperature. Steps (ii) and (iii) have no special temperature requirements; ambient room temperature is satisfactory. However, higher or lower temperatures may be used if desired.

Other values for $R_1$ and $R_2$ include phenyl, furfuryl, thiophenyl, pyridyl and their derivatives.

The following examples will serve to illustrate the practice of the invention in more detail. In Examples 1-7 sodium hypophosphite in HCl medium is used to reduce the germanium tetrachloride. In Examples 8-14 the germanium tetrachloride is reduced in hypophosphorous acid aqueous solution. In Examples 15-19 sodium hypophosphite in methanol is used for the reduction step. In Examples 20-23 the reduction is accomplished with aqueous hypophosphorous acid in methanol. In Example 24, hypophosphorous acid in ethanol is used; Example 25 uses hypophosphorous acid and acidic ethanol; Example 26 uses sodium hypophosphite with ethanol; Example 27 uses sodium hypophosphite and acidic ethanol. When aqueous hypophosphorous acid per se is used then HCl and/or alcohol are optional but preferred. Hydrochloric acid (and/or ethanol) can be used with a salt of hypophosphorous acid to generate the hypophosphorous acid in situ. In any case, even when hypophosphorous acid per se is used HCl is preferably present since it will accelerate the reaction and enhance the yield.

EXAMPLE 1

(a) Reduction of $GeCl_4$ with sodium hypophosphite. 20 g of $GeCl_4$ is added to a solution of 30 g of sodium hypophosphite in 100 ml of concentrated HCl. Heat at reflux for 1 hour and allow to cool to room temperature. The reduced mixture is reserved for subsequent use.

(b) Preparation of bis-beta-carboxy ethyl germanium sesquioxide from acrylic acid. Add 6.5 g of acrylic acid to the $GeCl_4$-reduced mixture obtained in step (a) at room temperature. After reacting under agitation for 4 hours, collect the separated solid by filtration. Hydrolyze the solid by dissolving in 70 ml of water and stirring at room temperature for 1 hour. Collect the crystals by filtration and wash with water and acetone successively. Dry in an oven (80°–100° C.) to give 8 g (50%) of the title compound.

The IR spectrum of the product shows absorption at 3300–2800, 1690, 1410, 1240 $cm^{-1}$ characteristic of COOH; and 900 and 800 $cm^{-1}$ characteristic of germanium sesquioxide. The spectrum is identical with the IR spectrum reported in Asai's book "Organic Germanium—A Medical Godsend" (Japanese edition) and also checks with marketed samples available from Asai Clinic.

The NMR spectrum ($D_2O$, NaOD) shows triplet peaks of same proton numbers at 1.6 and 2.5 ppm.

Elemental analysis for Ge: Calculated: 42.6%; Found: 41.8%.

EXAMPLE 2

Preparation of bis-beta-carboxy-beta-methyl ethyl germanium sesquioxide from methacrylic acid. Add 8 g of methacrylic acid to the $GeCl_4$-reduced mixture obtained in Example 1 step (a) at room temperature. After reacting under agitation for 4 hours, collect the separated solid by filtration. Hydrolyze the solid as in Example 1 step (b) to give 10 g (58%) of the title compound.

The IR spectrum shows characteristic absorption at 3450, 3300–2800, 1700, 1410, 1240 $cm^{-1}$ (COOH); and 880 and 800 $cm^{-1}$ (germanium sesquioxide).

The NMR spectrum ($D_2O$, NaOD) shows peaks at 1.2 ppm (d,3H); 1.6 ppm(q,2H); and 2.8 ppm(m,1H).

EXAMPLE 3

Preparation of bis-beta-carboxy-meta-methyl ethyl germanium sesquioxide from methyl methacrylate. Add 9.3 g of methyl methacrylate to the $GeCl_4$-reduced mixture obtained in Example 1(a) at room temperature. Keep the reaction under agitation for 4 hours, then extract the oily product with benzene. After removal of benzene by evaporation, the residue is hydrolyzed by dissolving in 70 ml of water and stirring at room temperature for 1 hour. Collect the crystals by filtration and wash with water and acetone successively. After drying in an oven (80°–100° C.), 5.5 g (32%) of the title compound is obtained. The IR spectrum is identical with that produced in Example 2.

EXAMPLE 4

Preparation of bis-beta-carboxy ethyl germanium sesquioxide from methyl acrylate. Add 8 g of methyl acrylate to the $GeCl_4$-reduced mixture obtained from Example 1 step (a) at room temperature. Keep the reaction under axitation for 4 hours, then extract the oily product with benzene. After removal of benzene by evaporation, the residue is hydrolyzed as in Example 3. Filter to collect 7 g of solid bis-beta-carboxy ethyl germanium sesquioxide (43% yield). The IR spectrum is identical with that produced in Example 1(b).

EXAMPLE 5

Preparation of bis-beta-carboxy-alpha-methyl ethyl germanium sesquioxide from crotonic acid. Add 8 g of crotonic acid to the $GeCl_4$-reduced mixture obtained in Example 1(a) at room temperature. After reacting under agitation for 4 hours, collect the solid by filtration. Hydrolyze the solid in water as in Example 1(b) to give 8.5 g (50%) of the title compound.

The IR spectrum shows characteristic absorption at 3300–2800, 1695, 1410, 1250 $cm^{-1}$ (COOH); and 900 and 790 $cm^{-1}$ (germanium sesquioxide).

EXAMPLE 6

Prepration of bis-beta-carboxy ethyl germanium sesquioxide from acrylonitrile. Add 4.9 g of acrylonitrile to the $GeCl_4$-reduced mixture obtained in Example 1(a) at room temperature. Keep the reaction under agitation for 4 hours, then extract the oily product with benzene. After the removal of benzene by evaporation, the residue is heated at reflux with 50 ml of concentrated hydrochloric acid for 1 hour and is further diluted with 100 ml of water after it is cooled down to room temperature. Collect the precipitate formed and wash with water and acetone successively and dry to give 4 g (25%) of the title compound. The IR spectrum is identical with that produced in Example 1(b).

EXAMPLE 7

Preparation of bis-beta-carboxy ethyl germanium sesquioxide from acrylamide. Add 5 g of acrylamide to the $GeCl_4$-reduced mixture obtained in Example 1(a) at room temperature. Keep the reaction under agitation for 4 hours. Filter to collect the solid, heat at reflux with concentrated hydrochloric acid and then hydrolyze in water as in Example 6 to give 5 g (30%) of the title compound. The IR spectrum is identical with that produced in Example 1(b).

EXAMPLE 8

(a) Preparation of $GeCl_4$-reduced solution by reduction of $GeCl_4$ with 50% hypophosphorous acid aqueous solution. Add 20 g of $GeCl_4$ to 38 g of 50% aqueous hypophosphorous acid solution. The reaction mixture is heated at reflux for 1 hour and allowed to cool to room temperature for later use.

(b) Preparation of bis-beta-carboxy ethyl sesquioxide from acrylic acid. Add 6.5 g of acrylic acid to the $GeCl_4$-reduced mixture obtained in step (a) at room temperature. After reacting under agitation for 4 hours, collect the separated solid by filtration. Hydrolyze the solid as in Example 1(b) to give 7 g (43%) of the title compound. The IR spectrum is identical with that produced in Example 1(b).

EXAMPLE 9

Preparation of bis-beta-carboxy-beta-methyl ethyl germanium sesquioxide from methacrylic acid. Add 8 g of methacrylic acid to the $GeCl_4$-reduced mixture obtained in Example 8, step (a) at room temperature. After reacting under agitation for 4 hours, collect the separated solid by filtration. Hydrolyze the solid in water as in Example 1, step (b) to give 8.5 g (50%) of the title compound. The IR spectrum is identical with that produced in Example 2.

EXAMPLE 10

Preparation of bis-beta-carboxy-beta-methyl ethyl germanium sesquioxide from methyl methacrylate. Add 9.3 g of methyl methacrylate to the $GeCl_4$-reduced mixture obtained in Example 8(a) at room temperature. After reacting under agitation for 4 hours, the oily product is extracted with benzene. After the removal of benzene by evaporation, the residue is hydrolyzed in water as in Example 3 to give 4.2 g (25%) of the title compound. The IR spectrum is identical with that produced in Example 2.

EXAMPLE 11

Preparation of bis-beta-carboxy ethyl germanium sesquioxide from methyl acrylate. Add 8 g of methyl acrylate to the $GeCl_4$-reduced mixture obtained in Example 8(a) at room temperature. After reacting under agitation for 4 hours, the oily product is extracted with benzene. Remove benzene by evaporation and hydrolyze the residue in water as in Example 3 to give 10 g of the title compound. The IR spectrum is identical to that produced in Example 1(b).

EXAMPLE 12

Preparation of bis-beta-carboxy-alpha-methyl ethyl germanium sesquioxide from crotonic acid. Add 8 g of crotonic acid to the $GeCl_4$-reduced mixture obtained in Example 8(a) at room temperature. After reacting under agitation for 4 hours, collect the separated solid by filtration. Hydrolyze the solid in water as in Example 1(b) to give 5 g (30%) of the title compound having an IR spectrum identical to that produced in Example 5.

EXAMPLE 13

Preparation of bis-beta-carboxy ethyl germanium sesquioxide from acrylonitrile. Add 4.9 g of acrylonitrile to the $GeCl_4$-reduced mixture obtained in Example 8(a) at room temperature. After reacting under agitation for 4 hours, the oily product is extracted with benzene. Concentrate to remove the solvent and hydrolyze the residue as in Example 6 by refluxing with concentrated hydrochloric acid and further dilute with water to give 5 g (31%) of the title compound having an IR spectrum identical to that produced in Example 1(b).

EXAMPLE 14

Preparation of bis-beta-carboxy ethyl germanium sesquioxide from acrylamide. Add 5 g of acrylamide to the $GeCl_4$-reduced mixture obtained in Example 8(a) at room temperature. After reacting under agitation for 4 hours, collect the separated solid by filtration. Hydrolyze the solid as in Example 6 by refluxing with concentrated hydrochloric acid and further dilute with water to give 3.8 g (24%) of the title compound having an IR spectrum identical to that produced in Example 1(b).

EXAMPLE 15

(a) Preparation of methanolic germanium solution. Dissolve 9.2 g of $GeCl_4$ in 70 ml of methanol. To this solution, add 100 ml of methanol containing 9 g of sodium hypophosphite. After reacting under agitation for 1 hour, filter off the formed NaCl and reserve the filtrate for subsequent use.

(b) Preparation of bis-beta-carboxy ethyl germanium sesquioxide from acrylic acid. Add 7 g of acrylic acid to the methanolic reduced-germanium solution obtained in step (a) at room temperature. After reacting under agitation for 4 hours, concentrate to remove the solvent. To this residue, add 100 ml of distilled water and 1 ml of concentrated HCl and continue the agitation for another 4 hours. Collect the solid by filtration to provide 6 g (82%) of the title compound having an IR spectrum identical to that produced in Example 1(b).

EXAMPLE 16

Preparation of bis-beta-carboxy-beta-methyl-ethyl germanium sesquioxide from methacrylic acid. Add 100 ml of methacrylic acid to the methanolic reduced-germanium solution obtained in Example 15, step (a) at room temperature. After reacting under agitation for 4 hours, concentrate to remove the solvent. To this residue, add 100 ml of distilled water and continue the agitation for another 4 hours. Collect the solid by filtration to provide 3 g (38%) of the title compound having an IR spectrum identical with that produced in Example 2.

EXAMPLE 17

Preparation of bis-beta-carboxy-alpha-methyl ethyl germanium sesquioxide from crotonic acid. Add 10 g of crotonic acid to the methanolic reduced-germanium solution obtained in Example 15(a) at room temperature. After reacting under agitation for 4 hours, concentrate to remove the solvent. To this residue, add 100 ml of distilled water and continue the agitation for another 4 hours. Collect the solid by filtration to provide 4.5 g (62%) of the title compound having an IR spectrum identical to that produced in Example 5.

EXAMPLE 18

Preparation of bis-beta-carboxy ethyl germanium sesquioxide from acrylonitrile. Add 5 g of acrylonitrile to the methanolic reduced-germanium solution obtained in Example 15(a) at room temperature. After reacting under agitation for 4 hours, concentrate to remove the solvent. To this residue, add 100 ml of distilled water and continue the agitation for another 4 hours. Collect the solid by filtration to provide 5 g (69%) of the title compound having an IR spectrum identical to that produced in Example 1(b).

EXAMPLE 19

Preparation of bis-beta-carboxy ethyl germanium sesquioxide from acrylamide. Add 7.4 g of acrylamide to the methanolic reduced-germanium solution obtained in Example 15(a) at room temperature. After reacting under agitation for 4 hours, concentrate to remove the solvent. To this residue, add 100 ml of distilled water and continue the agitation for another 4 hours. Collect the solid by filtration to provide 2 g (30.5%) of the title compound having an IR spectrum identical to that produced in Example 1(b).

EXAMPLE 20

(a) Preparation of aqueous methanolic reduced-germanium solution. Dissolve 9.2 g of $GeCl_4$ in 70 ml of methanol. To this solution add 100 ml of methanol which contains 5 ml of 50% hypophosphorous acid. After stirring for a period of 2 hours, the mixture is ready for subsequent use.

(b) Preparation of bis-beta-carboxy ethyl germanium sesquioxide from acrylic acid. Add 6.2 g of acrylic acid to the aqueous methanolic reduced-germanium solution obtained in step (a) at room temperature. After reacting under agitation for 4 hours, concentrate to remove the solvent. To this residue, add 100 ml of distilled water and continue the agitation for another 4 hours. Filter the crystals formed to obtain 3 g (42%) of the title compound having an IR spectrum identical to that of Example 1(b).

EXAMPLE 21

Preparation of bis-beta-carboxy-beta-methyl ethyl germanium sesquioxide from methacrylic acid. Add 10 ml of methacrylic acid to the aqueous methanolic reduced-germanium solution obtained in Example 20, part (a), at room temperature. After reacting under agitation for 4 hours, concentrate to remove the solvent. To this residue, add 100 ml of distilled water and continue the agitation for another 4 hours. Filter the crystals formed to obtain 4 g (50%) of the title compound having an IR spectrum identical to that of Example 2.

EXAMPLE 22

Preparation of bis-beta-carboxy-alpha-methyl ethyl germanium sesquioxide from crotonic acid. Add 10 g of crotonic acid to the aqueous methanolic reduced-germanium solution obtained in Example 20(a) at room temperature. After reacting under agitation for 4 hours, evaporate the solvent. To this residue, add 100 ml of distilled water and continue stirring for another 4 hours. Filter the crystalline product to obtain 3 g (38%) of the title compound having an IR spectrum identical to that of Example 5.

EXAMPLE 23

Preparation of bis-beta-carboxy ethyl germanium sesquioxide from acrylamide. Add 7.4 g of acrylamide to the aqueous methanolic reduced-germanium solution obtained in Example 20(a) at room temperature. After reacting under agitation for 4 hours, evaporate the solvent. To this residue, add 100 ml of distilled water and continue stirring for another 2 hours. The resultant mixture is extracted with 100 ml of ether three times, and then evaporated to remove the ether. To this residue again add 100 ml of distilled water and continue stirring for another 4 hours. Filter off the crystalline product to obtain 5 g (69%) of the title compound having an IR spectrum identical to that of Example 1(b).

EXAMPLE 24

Reduction of ethanolic germanium tetrachloride by hypophosphorous acid and further reacting with acrylic acid.

Dissolve 1.25 ml (1.5 g) of hypophosphorous acid in 25 ml of ethanol, then add 2.3 g of germanium tetrachloride. After stirring 2 hours, add 1.54 g of acrylic acid. Heat the resultant mixture in a water bath (70° C.) with stirring for 2 hours. After ethanol is removed by evaporation, add 10 ml of distilled water and continue stirring at room temperature for another 4 hours. Filter off the crystalline product to obtain 0.3 g (16%) of bis-beta-carboxy ethyl germanium sesquioxide having an IR spectrum showing the same results as in Example 1(b).

EXAMPLE 25

Reduction of germanium tetrachloride in acidic ethanol by hypophosphorous acid and further reacting with acrylic acid.

Dissolve 1.25 ml (1.5 g) of 50% hypophosphorous acid in 25 ml of ethanol which contains 2 ml of concentrated HCl, then add a solution of 2.39 g of germanium tetrachloride in 10 ml of ethyl alcohol. After stirring for 2 hours, add 1.54 g of acrylic acid and continue stirring for another 2 hours. After ethanol is removed by evaporation, add 10 ml of distilled water to this residue and stir for 4 hours at room temperature. Filter off the crystalline product to obtain 0.8 g (44%) of bis-beta-carboxy ethyl germanium sesquioxide having an IR spectrum as in Example 1(b).

EXAMPLE 26

Reduction of ethanolic germanium tetrachloride by sodium hypophosphite and further reaction with acrylic acid.

Suspend 2.6 g of sodium hypophosphite in 20 ml of ethanol. Add dropwise a solution of 2.3 g of GeCl$_4$ in 10 ml of ethanol. After stirring for 2 hours, filter off the precipitated produced. Add 1.54 g of acrylic acid to this filtrate and continue stirring at room temperature for another 4 hours. After ethanol is evaporated, add 10 ml of distilled water to the residue. This residue is hydrolyzed to give 0.5 g (27.5%) of bis-beta-carboxy ethyl germanium sesquioxide. The IR spectrum is the same as in Example 1(b).

EXAMPLE 27

Reduction of germanium tetrachloride in acidic ethanol by sodium hypophosphite and further reaction with acrylic acid.

Add 2.6 g of sodium hypophosphite to a solution of 20 ml of ethanol which contains 2 ml of concentrated HCl. The mixture is stirred for a period of ½ hour and filtered to remove the precipitate formed. An ethanolic solution containing 2.3 g of germanium tetrachloride is added and agitated for 2 hours. Then 1.54 g of acrylic acid is added and stirring is continued for another 4 hours. Evaporate the ethanol and hyrolyze the residue by adding 10 ml of distilled water. Filter to collect 0.4 g (22%) crystalline product, bis-beta-carboxy ethyl germanium sesquioxide. The IR spectrum is the same as that in Example 1(b).

What is claimed is:

1. A process for preparing an organo germanium sesquioxide derivative of the following formula (II):

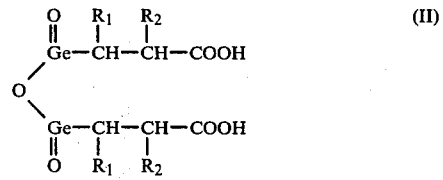

where $R_1$ and $R_2$ are independently hydrogen or lower alkyl, comprising in combination the steps of:
(i) reacting germanium tetrachloride with hypophosphorous acid or its salts, whereby the germanium tetrachloride is reduced,
(ii) thereafter adding to the reaction mixture an acrylic acid derivative of the following formula (I):

where $R_1$ and $R_2$ are as previously defined and Y is COOH, COOR (R being lower alkyl), CONH$_2$ or CN, and
(iii) hydrolyzing the product of step (ii) whereby the said compound of formula II is formed.

2. A process as in claim 1 in which step (i) is carried out at refluxing temperature.
3. A process as in claim 1 in which (I) is acrylic acid.
4. A process as in claim 1 in which (I) is methacrylic acid.
5. A process as in claim 1 in which (I) is methyl methacrylate.
6. A process as in claim 1 in which (I) is methyl acrylate.
7. A process as in claim 1 in which (I) is crotonic acid.
8. A process as in claim 1 in which (I) is acrylonitrile.
9. A process as in claim 1 in which (I) is acrylamide.
10. A process as in claim 1 in which step (iii) is carried out in the presence of water.
11. A process as in claim 1 in which step (iii) is carried out in the presence of water and hydrochloric acid.
12. The process of claim 1 wherein, in step (i), the hypophosphorous acid is formed by the reaction of sodium hypophosphite and hydrochloric acid.
13. The process of claim 1 wherein, in step (i), the germanium tetrachloride is reacted with aqueous hypophosphorous acid per se.
14. The process of claim 1 wherein, in step (i), the hypophosphorous acid is formed by the reaction of sodium hypophosphite with methanol or ethanol.
15. The process of claim 1 wherein, in step (i), the reaction is carried out with aqueous hypophosphorous acid in the presence of methanol or ethanol.
16. The process of claim 1 wherein, in step (i), the reaction is carried out with aqueous hypophosphorous acid in the presence of hydrochloric acid and methanol or ethanol.
17. The process of claim 1 wherein, in step (i), the germanium tetrachloride is reduced by a salt of hypophosphorous acid.

* * * * *